United States Patent
Mentzel et al.

(10) Patent No.: US 10,239,801 B2
(45) Date of Patent: *Mar. 26, 2019

(54) HYDROGEN REJECTION IN METHANOL TO HYDROCARBON PROCESS WITH BIFUNCTIONAL CATALYST

(71) Applicant: Haldor Topsøe A/S, Kgs. Lyngby (DK)

(72) Inventors: Uffe Vie Mentzel, Vanløse (DK); Finn Joensen, Hørsholm (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/768,631

(22) PCT Filed: Nov. 30, 2016

(86) PCT No.: PCT/EP2016/079280
§ 371 (c)(1),
(2) Date: Apr. 16, 2018

(87) PCT Pub. No.: WO2017/093320
PCT Pub. Date: Jun. 8, 2017

(65) Prior Publication Data
US 2018/0305275 A1    Oct. 25, 2018

(30) Foreign Application Priority Data

Nov. 30, 2015    (DK) .................... 2015 00768

(51) Int. Cl.
| | |
|---|---|
| *C07C 2/00* | (2006.01) |
| *C07C 2/86* | (2006.01) |
| *B01J 29/40* | (2006.01) |
| *C10G 53/14* | (2006.01) |
| *C10G 3/00* | (2006.01) |
| *B01J 29/90* | (2006.01) |
| *C01B 3/26* | (2006.01) |
| *B01J 23/00* | (2006.01) |
| *B01J 23/06* | (2006.01) |
| *B01J 38/12* | (2006.01) |

(52) U.S. Cl.
CPC ............. *C07C 2/862* (2013.01); *B01J 29/405* (2013.01); *B01J 29/90* (2013.01); *C01B 3/26* (2013.01); *C10G 3/49* (2013.01); *C10G 53/14* (2013.01); *B01J 23/005* (2013.01); *B01J 23/06* (2013.01); *B01J 38/12* (2013.01); *B01J 2229/20* (2013.01); *B01J 2229/42* (2013.01); *B01J 2523/00* (2013.01); *C01B 2203/0277* (2013.01); *C01B 2203/0405* (2013.01); *C01B 2203/1211* (2013.01); *C01B 2203/1217* (2013.01); *C07C 2529/40* (2013.01); *C10G 2400/02* (2013.01); *C10G 2400/20* (2013.01); *C10G 2400/30* (2013.01); *Y02P 20/52* (2015.11); *Y02P 20/584* (2015.11); *Y02P 30/20* (2015.11)

(58) Field of Classification Search
CPC ......... C07C 41/00; C07C 43/043; C07C 1/22; C07C 29/152; C07C 41/01; C10G 2400/02; C10G 3/45; C10G 3/49; C10G 50/00
See application file for complete search history.

(56) References Cited

U.S. PATENT DOCUMENTS

| | | |
|---|---|---|
| 4,013,732 A | 3/1977 | Chang et al. |
| 9,296,665 B2 * | 3/2016 | Kortan .................... C07C 41/00 |
| 2009/0071871 A1 | 3/2009 | Joensen et al. |
| 2010/0041932 A1 | 2/2010 | Dodwell et al. |
| 2013/0165725 A1 | 6/2013 | Chewter et al. |
| 2013/0261361 A1 | 10/2013 | Blommel et al. |
| 2014/0171691 A1 | 6/2014 | Kortan et al. |

FOREIGN PATENT DOCUMENTS

| | | |
|---|---|---|
| CN | 104557416 A | 4/2015 |
| CN | 104557432 A | 4/2015 |
| WO | WO 99/20712 A1 | 4/1999 |
| WO | WO 2007/020068 A1 | 2/2007 |
| WO | WO 2016/116612 A1 | 7/2016 |

* cited by examiner

*Primary Examiner* — Sharon Pregler
(74) *Attorney, Agent, or Firm* — Blank Rome LLP

(57) ABSTRACT

The present application relates to a process for production of hydrocarbons comprising the steps of: converting a feed stream comprising alcohols, ethers or mixtures hereof over a Zn-containing zeolite based catalyst wherein Zn is at least partly present as $ZnAl_2O_4$, active in dehydrogenation of hydrocarbons, in a conversion step thereby obtaining a conversion effluent, separating said effluent to obtain an aqueous process condensate stream, a liquid hydrocarbon stream and a gaseous stream, removing part of the hydrogen formed in the conversion step, and recycling at least part of the gaseous and/or liquid hydrocarbon stream to the conversion step.

30 Claims, 3 Drawing Sheets

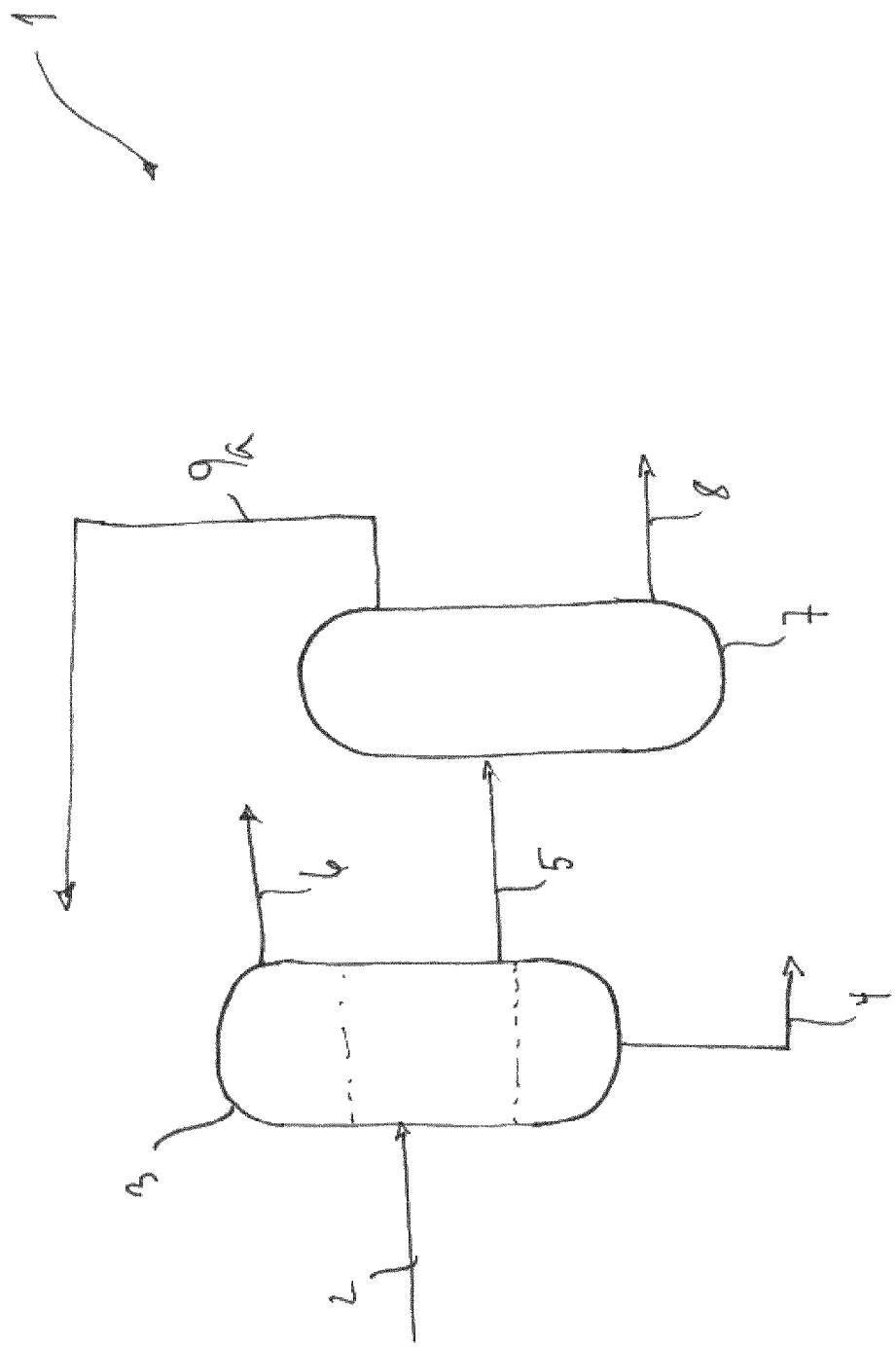

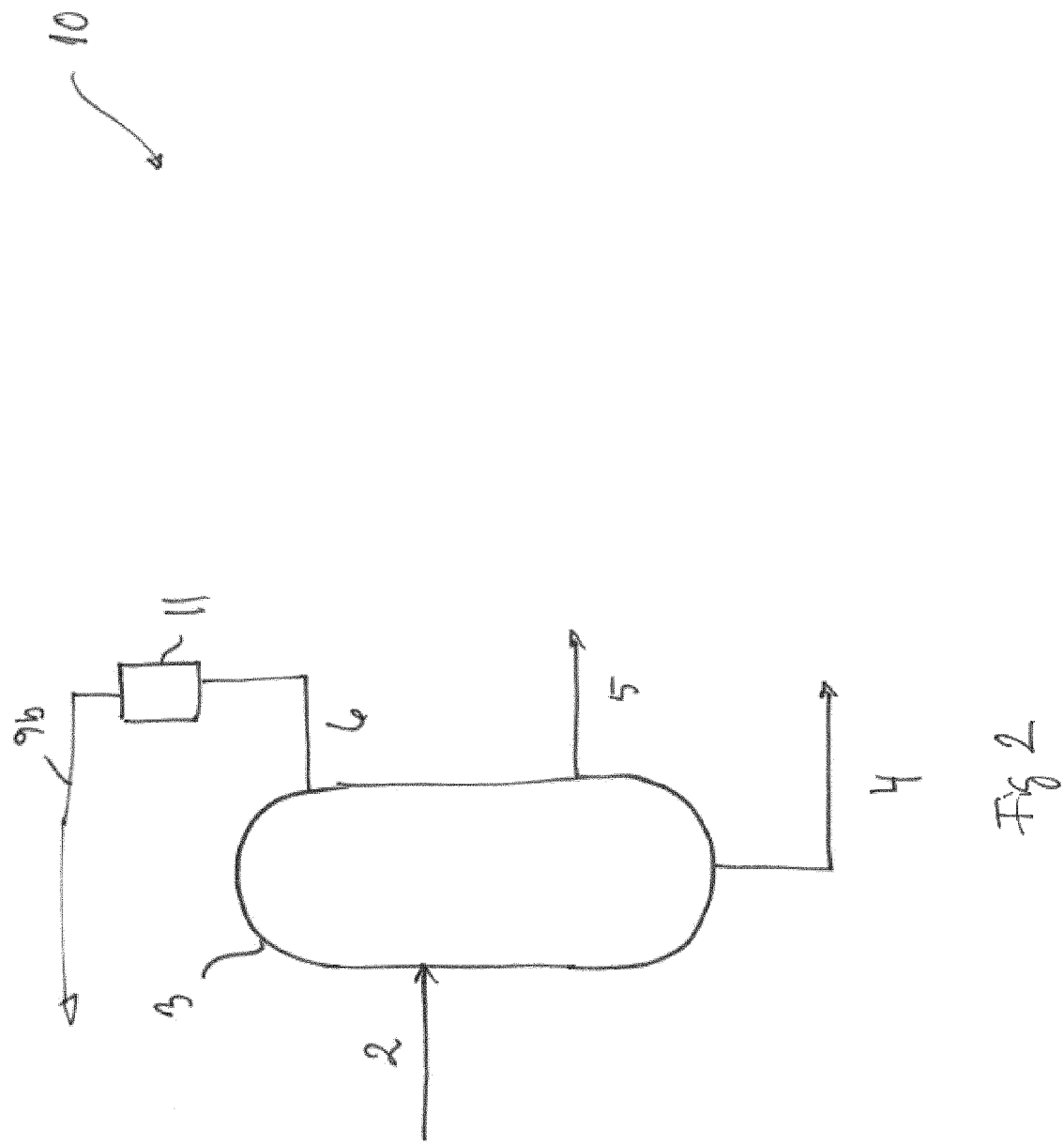

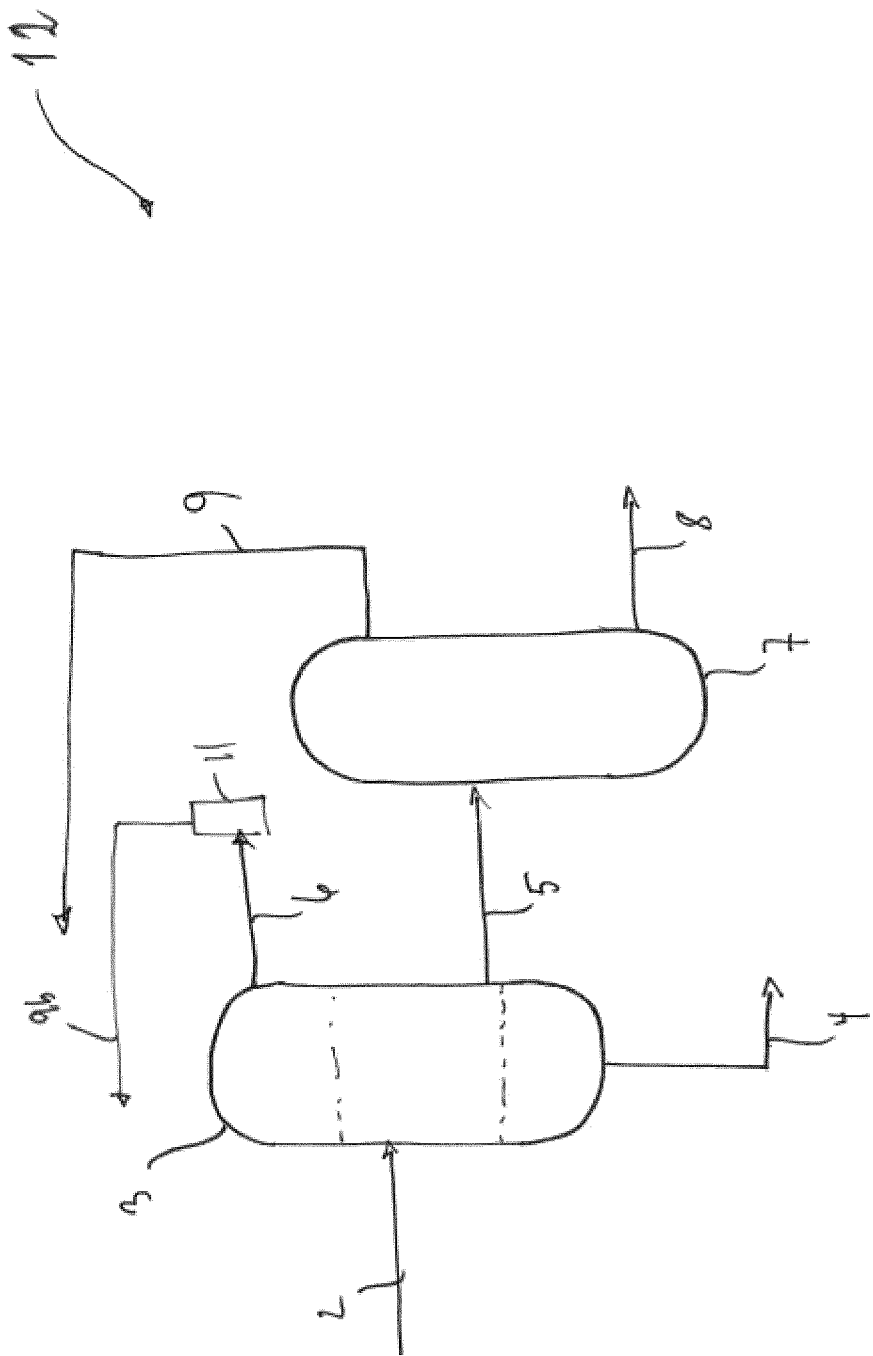

HYDROGEN REJECTION IN METHANOL TO HYDROCARBON PROCESS WITH BIFUNCTIONAL CATALYST

The conversion of methanol (MeOH) and/or dimethyl ether (DME), into hydrocarbon fuels and chemicals is of significant industrial importance. Prominent examples comprise methanol-to-gasoline (MTG) and methanol-to-olefins (MTO) processes.

In general, any alcohol or ether may be converted into hydrocarbons by these processes, but methanol is the preferred feedstock, because it may be produced in large scale and with high efficiency from any carbon-containing resource, such as coal, biomass, waste and natural gas. Prior to the conversion into hydrocarbons the methanol or alcohol feed may be converted, at least partially, into its ether analogue e.g. methanol to DME.

Similar processes have been disclosed for the conversion of alcohols into hydrocarbons, targeting different products such as aromatics.

The MTG process typically provides high-octane synthetic gasoline in excellent yields, close to about 90 percent by weight of the total amount of hydrocarbons produced and with typical octane numbers close to 90, expressed in terms of (R+M)/2 (Research Octane Number (RON)+Motor Octane Number (MON)/2). The synthetic gasoline typically contains substantial amounts of aromatics which contribute significantly to the octane number. Even higher octane numbers may be obtained by increasing the aromatics content, e.g. by increasing the pressure or temperature in the gasoline synthesis reactor or by reducing the space velocity. Changing synthesis conditions to improve aromatics selectivity, and thereby octane, however, imposes a penalty in terms of a reduced gasoline yield, because the formation of aromatics is inherently accompanied by increased selectivity to paraffins, in particular, propane and butanes which only to a limited extent may be added to the gasoline product slate due to their relatively high vapour pressures. In other words, the existing choice is between making a low-aromatics product in high yields or a high-aromatics product in low yields.

In a first aspect of the present invention is provided a process and plant for producing a hydrocarbon product with enhanced aromatics selectivity without simultaneously increasing the selectivity to light paraffins such as propane and butanes.

In a second aspect of the present invention is provided a process for the production of gasoline with improved yield and octane number.

In a third aspect of the present invention is provided a process for making a highly aromatic product.

These and other advantages are provided by a process for production of hydrocarbons comprising the steps of
  converting a feed stream comprising alcohols, ethers or mixtures hereof over a bifunctional catalyst comprising zeolite, alumina binder and Zn, wherein the Zn is present at least partly as $ZnAl_2O_4$, active in dehydrogenation of hydrocarbons, in a conversion step thereby obtaining a conversion effluent,
  separating said effluent to obtain an aqueous process condensate stream, a liquid hydrocarbon stream and a gaseous stream,
  removing part of the hydrogen formed in the conversion step, and
recycling at least part of the gaseous and/or liquid hydrocarbon stream to the conversion step.

I.e. according to the present invention there is provided a process for making a hydrocarbon product in which hydrogen produced in the conversion step is removed or partially removed from the synthesis loop, either by purging part of the gaseous recycle stream, hereinafter referred to as passive $H_2$ rejection, or by removing, partially or completely, $H_2$ from one or more recycle streams, hereinafter referred to as active $H_2$ rejection, in order to provide an at least partly $H_2$ depleted recycle. In the process e.g. methanol is converted over a preferably acidic zeolite based catalyst, combined with a metal or metal oxide component active in the dehydrogenation of hydrocarbons, into a conversion effluent comprising aromatics.

The conversion effluent is separated into a gaseous stream, an aqueous process condensate and a liquid hydrocarbon stream comprising a hydrocarbon product.

By the present process and plant wherein hydrogen is removed it is thus possible to increase the aromatics selectivity and at the same time reduce the selectivity to light paraffins, such as propane and butanes.

When the process is carried out with a bifunctional catalyst for conversion of oxygenates and dehydrogenation of hydrocarbons, said catalyst comprising zeolite, alumina binder and Zn, wherein the Zn is present at least partly as $ZnAl_2O_4$ the aromatics yield is increased compared to a standard catalyst without Zn. Furthermore, the applicant has shown that the selectivity of the catalyst is increased with the spinelization degree of the catalyst.

To increase the yield of aromatics, a bifunctional catalyst containing acidic zeolite sites as well as dehydrogenation sites e.g. metal or oxide is provided. This means that a stream comprising one or more oxygenates e.g. methanol may be converted in the presence of the catalyst into aromatics by the zeolite while dehydrogenation of hydrocarbons such as naphthenes, paraffins and/or isoparaffins, into olefins and/or aromatics also takes place.

In preferred embodiments the catalyst is optimized for conversion of oxygenates such as Methanol and/or DME into aromatics (herein abbreviated MTA).

The binder may be a pure alumina binder or an alumina-based binder further comprising mixtures of aluminum oxide and aluminum hydroxide and/or e.g. silica/alumina.

The zeolite may for example be one of the commonly known zeolites used in MTA and MTG processes. For example, H-ZSM-5 may be a preferred zeolite for the present catalyst due to its unique pore structure leading to favorable size selectivity as well as its relatively low coking rate. H-ZSM-5 may be particularly preferred in case of MTA processes.

Examples of Zn/ZSM-5 catalysts with low content of Zn such as 1 wt % Zn for MTA are known and it has been argued that higher Zn content is to be avoided in order to avoid methanol cracking to carbon oxides. However, the applicant has shown that a high Zn content in the catalyst may result in an improved aromatics yield in MTA processes compared to known catalysts. Thus, in several advantageous embodiments the total Zn content in the catalyst is 3-25 wt %, 5-20 wt %, 7-15 wt % or 8-13 wt %, such as more than 7 wt % Zn, more than 10 wt % Zn or 12 wt % or more Zn.

Depending on the production process the Zn in the catalyst may be present in various concentrations in both binder and zeolite of the present catalyst. E.g. in some embodiments the Zn concentration is higher in the binder phase than in the zeolite phase which for example may be the case where the Zn is applied by impregnation.

A catalyst wherein Zn is present in both zeolite and alumina binder allows for industrial production by "simple"

means such as by impregnation. For example, a bifunctional catalyst as herein described may be achieved by Zn impregnation of a "base catalyst" comprising an alumina binder and a zeolite such as ZSM-5. A preferred base catalyst comprises 30-50% binder and 50-70% zeolite.

The impregnation may be carried out by contacting the zeolite or the zeolite and alumina binder with a Zn-containing solution. The solution may preferably be aqueous, but other solvents than water may be preferred as well. Impregnation may also be carried out by contacting the zeolite or the zeolite and alumina binder with a solid Zn compound, e.g., by mixing and/or grinding or other treatments to ensure intimate mixing of the components.

The Zn source may be any Zn-containing, organic and/or inorganic, compound. Preferred compounds comprise zinc nitrate, zinc acetate and zinc oxide, hydroxide, carbonate or mixtures hereof.

In order to provide a functional catalyst, the impregnation will typically be followed by calcination or similar treatment(s).

However, when a zeolite or an alumina/zeolite based catalyst is impregnated with Zn in order to obtain the desired amount of Zn in the zeolite, significant amounts of Zn may also be introduced into the binder, for example, as ZnO and/or $ZnAl_2O_4$. Various ratios of $ZnO/ZnAl_2O_4$ may be achieved depending on the treatment of the impregnated catalyst.

The applicant has shown that in a desirable catalyst Zn in the alumina binder is present mainly as $ZnAl_2O_4$. Defining the relative amount of zinc oxide, ZnO, in the binder phase as molar percentage of Zn present as ZnO relative to the total amount of Zn contained in the binder phase it may be desirable to have a catalyst where the amount of ZnO present in the binder phase as less than 50%, or preferably less than 10%, such as less than 5% or less than 2%, preferably less than 1%, such as 0.5% or less than 0.1% ZnO.

I.e. it may be preferred that the Zn in the binder has been fully spinelized, according to the reaction equation $ZnO+Al_2O_3 \rightarrow ZnAl_2O_4$, meaning that all or substantially all of the Zn in the binder is present as $ZnAl_2O_4$.

Preferably a large part of the Zn in the alumina binder is present as $ZnAl_2O_4$. Defining the relative amount of $ZnAl_2O_4$ in the binder phase as molar percentage of Zn present as $ZnAl_2O_4$ relative to the total amount of Zn contained in the binder phase, in some embodiments 50-100% of the Zn in the binder is present as $ZnAl_2O_4$, for example more than 60%, more than 70% or more than 80%. In some advantageous embodiments 85-100% of the Zn in the binder is present as $ZnAl_2O_4$, such as more than 90% or more than 95%.

As shown by the applicant cracking of MeOH may be avoided with a high degree of spinelization, it may be preferred especially in case of high Zn content in the catalyst that more than 97% of the Zn in the binder is present as $ZnAl_2O_4$, such as more than 98%, more than 99%, more than 99,5% or more than 99,8% of the Zn in the binder is present as $ZnAl_2O_4$. Optimal and practically achievable $ZnAl_2O_4$ content ranges may be 95-100% in the binder is present as $ZnAl_2O_4$, such as 97%-99.9% Zn in the binder is present as $ZnAl_2O_4$.

In preferred embodiments the catalyst has been fully spinelized meaning that all or substantially all of the Zn in the binder is present as $ZnAl_2O_4$.

ZnO in the binder is active in cracking methanol which is an undesired reaction in MTA. Depending on the means of production and after-treatment of the catalyst more or less of the Zn in the alumina binder may be present as $ZnAl_2O_4$.

Steaming or calcination of a Zn impregnated catalyst as commonly applied in production of metal/zeolite systems may result in a partial spinelization of the Zn ($ZnO+Al_2O_3 \rightarrow ZnAl_2O_4$). However, it has been shown that with a high Zn content even a relatively high degree of spinelization may lead to substantial MeOH cracking, but that a very desirable catalyst is achieved with a high degree of or preferably full spinelization of Zn in the alumina binder i.e. where all or substantially all of Zn in the binder is present as $ZnAl_2O_4$.

A bifunctional catalyst where all of or substantially all Zn in the binder is present as $ZnAl_2O_4$ and where substantially no ZnO is present in the binder as described herein exhibits a low selectivity to $CO_x$ even if the Zn content is high e.g. above 9 wt %. Thus, in preferred embodiments the fresh (start of run) catalyst has a $CO_x$ selectivity (determined at 420° C., 20 bar, 10 mol % methanol and a WHSV of 1.6) below 8% preferably below 7% such as 6% or below, or 5% or lower, or even 2% or lower. The $CO_x$ selectivity is defined as the molar percentage of methanol in the feed converted into CO and $CO_2$ according to the net reactions:

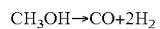

$$CH_3OH \rightarrow CO+2H_2$$

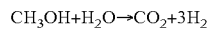

$$CH_3OH+H_2O \rightarrow CO_2+3H_2$$

Thus, by the present application is provided a preferred bifunctional catalyst comprising alumina binder, H-ZSM-5 and 8-15 wt % Zn in the total catalyst and where the Zn in the binder is fully or substantially fully spinelized. Said catalyst provides a high aromatics yield in a MTA reaction while cracking of the methanol is reduced to below 7%.

An exemplary bifunctional catalyst may desirably comprise 30-65 wt % H-ZSM-5, 5-40 wt % $ZnAl_2O_4$, 0-40 wt % $Al_2O_3$, 0-10 wt % ZnO.

The catalyst may further in some embodiments be characterized by having 0.1-12 wt % such as 1-7 wt % Zn present in the zeolite phase.

Alternatively, it may comprise 50-60 wt % H-ZSM-5, 10-35 wt % $ZnAl_2O_4$, 2-25 wt % $Al_2O_3$, 0-7 wt % ZnO. In order to avoid the presence of free ZnO in the binder phase, it may be beneficial to have at least a small excess of $Al_2O_3$ which is not spinelized in reaction with ZnO. Using a higher amount of $Al_2O_3$ in the preparation of the "base catalyst" will lead to a more robust catalyst preparation process.

Due to gradual coking of the catalyst during operation the catalyst must be regenerated at intervals in a stream comprising $O_2$.

A partially spinelized catalyst with a moderate to high $ZnAl_2O_4$:ZnO content may e.g. be obtained by heating the Zn-impregnated base catalyst at 300-500° C. in air.

A partially spinelized catalyst with a very high $ZnAl_2O_4$:ZnO content, fully spinelized catalyst or a substantially fully spinelized catalyst may be obtained by heating the Zn impregnated catalyst at 300-550° C. in steam or in an atmosphere comprising at least 10 vol %, 30 vol % 50 vol % or 80 vol % steam.

A partially spinelized catalyst with a very high $ZnAl_2O_4$:ZnO content, fully spinelized catalyst or a substantially fully spinelized catalyst may be obtained by heating a partially spinelized catalyst at 300-550° C. in steam or in an atmosphere comprising at least 10 vol %, 30 vol % 50 vol % or 80 vol % steam.

An at least partially spinelized catalyst, preferably a partially spinelized catalyst with a very high $ZnAl_2O_4$ content, a fully spinelized catalyst or a substantially fully spinelized catalyst as described herein may be provided in numerous ways including obtaining a desired spinelized catalyst during production or by producing a catalyst with a spinelization degree below the desired spinelization percentage and followed by steaming said catalyst in a subsequent step e.g. as in an in situ steaming step to obtain a catalyst with a desired degree of spinelization.

Various methods may be applied to produce the bifunctional catalyst: The two components (Zn and Zeolite) may constitute an integrated entity, e.g. as obtained by introducing the Zn component by impregnation or ion-exchange to the zeolite, either onto the zeolite itself or onto an extrudate in which the zeolite is embedded in an alumina binder. The Zn component may also be added in the form of a salt, either as a solid or in solution, or an oxide, hydroxide or carbonate together with the zeolite, binder and/or lubricants prior to shaping, e.g. during extrusion or pelletization.

The post-impregnation treatment (calcination or similar heat treatment) is preferably carried out in a humid atmosphere, e.g., by heating the Zn impregnated base catalyst at 300-550° C. in steam or in an atmosphere comprising at least 10 vol %, 30 vol % 50 vol % or 80 vol % steam.

Also physical mixtures of several acidic and metal components may be applied and the mixture may be charged to the reactor to form a uniform mixture or to form alternating layers or they may be graded to various degrees.

Methanol to Aromatics

The obtained hydrocarbon stream may be rich in aromatics, in which case the process hereinafter is referred to as a methanol-to-aromatics (MTA) process.

In the MTA conversion process methanol and/or other oxygenates is converted into aromatics while dehydrogenation of hydrocarbons including one or more types of hydrocarbons, comprising naphthenes, paraffins and isoparaffins, into olefins and/or aromatics is taking place.

The MTA conversion process may preferably be carried out at a pressure 5-60 bar, preferably 10-40 bar, temperature 300-500° C., preferably 330-480° C. and/or weight hourly space velocities (kg alcohol and/or ether feed per kg of catalyst per hour) between 0.1 and 10 preferably 0.3-3.

The MTA process may provide a product particularly suited as feedstock for downstream aromatics processing, e.g. for making para-xylene.

Methanol to Gasoline

The obtained hydrocarbon stream from the present process may comprise raw gasoline, in which case the process hereinafter is referred to as a methanol-to-gasoline (MTG) process.

In the MTG conversion process methanol is converted into a raw gasoline comprising aromatics, naphthenes, paraffins and isoparaffins and olefins while dehydrogenation of hydrocarbons including one or more types of hydrocarbons, comprising naphthenes, paraffins and isoparaffins, into olefins and/or aromatics is taking place.

The MTG conversion process may preferably be carried out at a pressure 5-60 bar, preferably 10-40 bar, temperature 300-500° C., preferably 300-430° C. and weight hourly space velocities (kg alcohol and/or ether feed per kg of catalyst per hour) between 0.1 and 10 preferably 0.5-3.

Hydrogen Rejection

The dehydrogenation reaction, promoting the formation of aromatics, is equilibrium-limited and in a synthesis loop, hydrogen may build up until the dehydrogenation reaction becomes essentially extinct.

Therefore, removal of hydrogen from the loop ensures that the dehydrogenation reaction is sustained. The hydrogen removal may be continuous, carried out in intervals and/or determined by preselected or adapted desired $H_2$ concentrations e.g. in depleted or partially depleted recycle stream(s).

According to the invention $H_2$ may be at least partly removed by one or more methods removing $H_2$ at one or more stages, from one or more streams.

As mentioned above, removal of $H_2$ from the synthesis loop may be passive, i.e. by purging part of the gaseous recycle stream, or active, to be understood as methods by which one or more recycle streams are selectively depleted or partially depleted with respect to $H_2$.

Depending on the method used for $H_2$ removal more or less $H_2$ may be removed. Also, the selectivity in the removal towards $H_2$ may vary. For example, if a permselective membrane is used for the removal the membrane may allow other substances than $H_2$ such as methane and carbon monoxide to pass through in which case not only $H_2$ is removed. Similarly, e.g. oxidation steps may result in oxidation of other substances than $H_2$, e.g. carbon monoxide.

According to some embodiments an at least partially $H_2$ depleted recycle stream is obtained from the gaseous stream by passing the gaseous stream to a hydrogen perm-selective membrane. I.e. the gaseous stream is provided to a stage wherein the gas is passed to a membrane removing $H_2$. The permeation of $H_2$ in the selective membrane may be adjusted to leave a pre-determined amount of hydrogen in the retentate recycled to the conversion step as the at least partially $H_2$ depleted recycle stream.

Alternatively, the at least partially $H_2$ depleted recycle stream is obtained from the gaseous stream by passing said gaseous phase, after admixture with a predetermined amount of dioxygen, to a catalytic preferential oxidation, commonly known as PrOx, step where hydrogen is reacted with said predetermined amount of oxygen to form water and recycling said reacted stream, at least partially depleted in hydrogen, to the conversion step. The catalytic oxidation is preferably carried out at essentially the same pressure as in the conversion step at a temperature between 50 and 300° C., preferably, 100-200° C. Catalysts effective in selective oxidation typically comprise a noble metal supported on an inorganic metal oxide.

Optionally, the at least partially $H_2$ depleted recycle stream is obtained from the gaseous stream by passing said gaseous phase, after admixture with a predetermined amount of a non-dioxygen hydrogen scavenger, to a catalytic oxidation step where hydrogen is reacted with said predetermined amount oxidizing agent and recycling said reacted stream, at least partly depleted in hydrogen, to the conversion step.

The hydrogen scavenger may be an aldehyde or a ketone, in which case said aldehyde and hydrogen is converted into an alcohol over a hydrogenation catalyst. For example, the aldehyde may be formaldehyde in which case formaldehyde and hydrogen is converted into methanol over a hydrogenation catalyst.

The hydrogen scavenger may be hydrogen peroxide in which case hydrogen peroxide and hydrogen is converted into water over a hydrogenation catalyst.

The separation step, where the effluent from the conversion step is separated into a gas phase and aqueous and hydrocarbon liquid phases, is typically conducted by cooling the conversion effluent essentially at the synthesis pressure, at 10-50 bar, typically by cooling to a temperature between 30 and 80° C. Under these conditions $H_2$ is almost only found in the gaseous phase in the separator, and the liquid hydrocarbon (as well as the aqueous phase) is almost completely $H_2$ free. This means that the liquid hydrocarbon phase may be separated into a product phase and one or more lower- and/or higher-boiling phases, and at least one of the lower- and/or higher-boiling phases can then at least partially be recycled to the conversion step as one of one or more at least partially H$_2$ depleted recycle.

Thus, several embodiments according to the present invention have been proposed, wherein hydrogen may be removed from the synthesis loop and thereby enhance the selectivity to aromatics. Other means of promoting the selectivity to aromatics for example includes increasing the temperature in the conversion reactor, thereby thermodynamically favouring the dehydrogenation reaction and, in turn, enhancing the selectivity to aromatics.

The degree of H$_2$ removal affects the products from the conversion. As mentioned above, if no means of hydrogen removal is established, hydrogen will accumulate in the loop and, eventually, the dehydrogenation reaction will cease. Therefore, continuous removal of hydrogen from the loop may be required in order to sustain the dehydrogenation reaction. To which extent yield and selectivity may be increased depends on how much hydrogen is rejected from the synthesis loop. Thus, if only a limited part of the hydrogen is rejected, e.g. purging part of the recycle gas (passive rejection) this will lead to a product with a slight enrichment in aromatics, whereas a high degree of hydrogen rejection, as may be achieved by active H$_2$ rejection as described above, will provide a product with a high aromatics content and even with aromatics as the main constituent.

The extent of hydrogen removal, therefore, represents a convenient and efficient tool for controlling aromatics selectivity and product yield.

In a methanol-to-gasoline context removal of hydrogen, passive or active, will lead to a higher gasoline yield as well as improved octane due the enhanced selectivity to aromatics. However, in most areas the aromatics content is regulated, typically to 35 vol % (some 40 wt %), which imposes a limit to how much hydrogen may be removed. Nonetheless, a few per cent improvement in gasoline yield and at the same time gaining a few numbers in octane represents a significant economic advantage. Moreover, as will be shown by examples, the selectivity to heavy oil (carbon number C11 and higher) and durene (1,2,4,5 tetramethylbenzene) is significantly reduced by the present process. I.e. the invention provides for making gasoline with improved yield and octane and with reduced selectivity to heavy oil and durene.

In an MTA context, there is no limit as to how much hydrogen should be removed and aromatic yields in the order of 70% or more may be achieved at close to complete hydrogen rejection.

The selectivity to aromatics increases with temperature, in part due to higher rates of reaction, but primarily, because dehydrogenation becomes favoured thermodynamically by an increase in temperature. Consequently, higher aromatic yields may be obtained by conducting the conversion at higher temperatures.

Thus the present process provides a method for making hydrocarbons wherein the content of aromatics in the product slate may be controlled to a significant extent by applying a catalyst or a combination of catalysts active in dehydrogenation and methanol-to-hydrocarbons formation and a means of passive or active rejection of hydrogen from the synthesis loop, the degree of which passive and/or active, controls the amount of aromatics in the product slate.

The feed stream may comprise methanol, dimethyl ether or mixtures hereof.

In preferred setups the process is carried out in a fixed bed reactor.

Thus, in summary a highly advantageous process is achieved by the present invention wherein the advantages of the H$_2$ removal from the process loop is fully utilized together with the bifunctional catalyst preferably having a high Zn content e.g. >8 wt % as well as a high degree of spinelization of the Zn in the alumina binder and thereby a reduced COx selectivity resulting in a reduced H$_2$ formation from MeOH cracking. I.e. in some aspects of the present process is provided a process for production of hydrocarbons with increased aromatics content due to the H$_2$ reducing features of the process and catalyst.

EXAMPLE 1

Preparation of Catalyst

A base catalyst containing 65 wt % H-ZSM-5 and 35% Al$_2$O$_3$ was prepared by mixing followed by extrusion following well known procedures. Upon calcination, samples of the base catalyst were impregnated with an aqueous solution containing zinc nitrate at different Zn concentrations. The resulting pore-filled extrudates were heated to 470° C. in air and kept at 470° C. for 1 h to obtain catalysts with various amounts of Zn.

EXAMPLE 2

Catalyst Activity and Regeneration

Catalysts prepared by the procedure described in example 1 were subjected to conversion of methanol at 420° C. in an isothermal fixed bed reactor. N$_2$ was used as an inert co-feed to obtain a methanol concentration of 7 mol % in the reactor inlet. The total pressure was 20 bar, and the space velocity (WHSV) of methanol was 2 h$^{-1}$.

Zn/H-ZSM-5 catalysts suffer from reversible as well as irreversible deactivation. Deposition of carbon (coke) on the catalyst is responsible for reversible deactivation. In the example shown in table 1, the deactivated (coked) catalyst is regenerated by removal of the deposited carbon by combustion in a flow of 2% O$_2$ (in N$_2$) at 500° C.

Due to irreversible deactivation, the catalyst did not fully regain its activity after regeneration. The results in table 1 show, that a catalyst containing 10% Zn is able to regain significantly more of its original activity after regeneration than a catalyst containing 5% Zn.

TABLE 1

Catalyst activity after regeneration. Wt % of aromatics in hydrocarbon product is defined as the mass of aromatics relative to the total mass of hydrocarbons in the effluent stream.

| Zn content (wt %) | Aromatics in total hydrocarbon product (wt %) | Percentage of aromatics selectivity regained after regeneration |
|---|---|---|
| 5 | 52 | 90 |
| 10 | 51 | 95 |

EXAMPLE 3

Stability Towards Steaming

To simulate catalyst activity after extended operation under industrial conditions, the catalysts were subjected to methanol conversion after steaming under severe conditions. Methanol conversion was performed under the same conditions as in example 2. The results in Table 2 show that the catalyst containing 10% Zn retains significantly more of its original activity than the catalyst containing 5 wt % Zn after severe steaming.

TABLE 2

Loss of catalyst activity upon severe steaming (100% steam for 48 h at 500° C. and 1 bar). Wt % of aromatics in hydrocarbon product is defined as the mass of aromatics relative to the total mass of hydrocarbons in effluent stream.

| Zn content (wt %) | Aromatics in hydrocarbon product (wt %), fresh catalyst | Aromatics (wt %) in hydrocarbon product, steamed catalyst |
|---|---|---|
| 5 | 52 | 28 |
| 10 | 51 | 36 |

EXAMPLE 4

Methanol Cracking vs. Zn Content

Cracking (decomposition) of methanol/DME can occur via several mechanisms. For example, the acidic sites in the catalyst may catalyze cracking of DME to $CH_4$, CO, and $H_2$, while certain Zn species catalyze cracking of methanol to CO and $H_2$. $CO_2$ can be formed as a primary cracking product or indirectly via the water gas shift reaction.

When methanol is converted over a catalyst containing Zn, part of the methanol is converted to COx due to cracking, which results in lower yield of hydrocarbon products. Methanol conversion has been performed at 420° C., 20 bar, 10 mol % methanol (N2 balance), and a space velocity (WHSV) of 1.6.

The results in Table 3 were obtained using catalysts prepared according to example 1. The results show that the cracking activity is highly dependent on the amount of Zn, i.e. higher Zn content leads to higher cracking activity.

TABLE 3

$CO_x$ selectivity at different contents of Zn

| Zn content (wt %) | $CO_x$ selectivity (%) |
|---|---|
| 0 | <0.1 |
| 3 | 2 |
| 5 | 4 |
| 10 | 9 |

EXAMPLE 5

COx Selectivity After Calcination and Steaming

A base catalyst containing 65% ZSM-5 and 35% $Al_2O_3$ was impregnated with aqueous zinc nitrate solution. The resulting pore filled extrudates were calcined in air and steam, respectively. Furthermore, the catalyst calcined in air was subjected to steaming after calcination. Methanol conversion over these catalysts was performed using the same conditions as in example 4.

The results in table 4 show that the presence of steam during calcination of the impregnated catalyst or heating the catalyst in the presence of steam after calcination leads to lower selectivity to $CO_x$. This observation may be rationalized by the fact that the presence of steam leads to formation of $ZnAl_2O_4$ rather than free ZnO in the binder phase.

TABLE 4

$CO_x$ selectivity for catalysts containing 10% Zn, calcined in the presence of different amounts of steam

| Condition | $CO_x$ selectivity (%) |
|---|---|
| Calcined in air | 9 |
| Calcined in steam (500° C., 2 h) | 2 |
| Calcined in air, steamed after calcination (500° C., 5 h) | 4 |
| Calcined in air, steamed after calcination (500° C., 48 h) | <0.1 |

EXAMPLE 6-8

Examples 6-8 demonstrate the influence of hydrogen on yield and selectivity. A reference experiment with un-doped H-ZSM-5 (example 6) was conducted at 420° C. and a weight hourly space velocity of 1.6. Example 6 was then repeated, except that a Zn-impregnated catalyst containing 2.9 wt % zinc was applied (example 7). Finally, example 7 was repeated, but this time the nitrogen carrier gas was replaced by a mixture of 5 vol % hydrogen in nitrogen (example 8).

The results of the three experiments, averaging a period of 30 hours are reported in Table 5.

TABLE 5

| Example | 6 | 7 | 8 |
|---|---|---|---|
| Temperature (° C.) | 420 | 420 | 420 |
| Pressure (bar g) | 20 | 20 | 20 |
| WHSV | 1.6 | 1.6 | 1.6 |
| Carrier gas (vol % $H_2/N_2$) | 0/100 | 0/100 | 5/95 |
| Average over period (hrs) | 0-30 | 0-30 | 0-30 |
| Products (wt % of total HC) | | | |
| n-paraffins | 27.30 | 12.45 | 14.31 |
| i-paraffins | 27.86 | 24.52 | 29.89 |
| Olefins | 7.92 | 13.79 | 9.04 |
| Naphthenes | 1.30 | 2.56 | 2.94 |
| Aromatics | 35.18 | 46.50 | 43.72 |
| C11+ ("heavy oil") | 0.61 | 0.58 | 0.38 |
| Overall molar H/C ratio in hydrocarbon product | 2.01 | 1.83 | 1.89 |
| Overall C5+ yield | 50.50 | 66.99 | 65.98 |
| Aromatics in C5+ fraction | 69.91 | 69.38 | 66.25 |
| Olefins in C5+ fraction | 1.76 | 3.76 | 2.11 |
| Durene in C5+ fraction | 1.48 | 2.54 | 1.96 |

By comparing example 7 with reference example 6 it is again shown that incorporation of Zn to the H-ZSM-5 catalyst leads to a significant improvement in yield and aromatics selectivity. The effect of hydrogen at the inlet of the reactor is demonstrated by comparing example 7 and 8, showing that the presence of hydrogen causes a decline in the aromatics selectivity and a slight reduction in the $C_{5+}$ yield. However, when comparing example 8 with reference example 6 it is clear that, despite the presence of hydrogen, the $C_{5+}$ yield and aromatics selectivity is still significantly higher, showing that the Zn-doped catalyst is capable of improving yield and aromatics selectivity even when hydrogen is present at the reactor inlet. This demonstrates that, in a synthesis loop, controlling the amount of hydrogen recycled to the conversion reactor inlet provides a means of directing the selectivity towards aromatics.

It is also observed (example 7 & 8) that the presence of hydrogen reduces the formation of durene and heavy oil. At the high temperatures applied in examples 6-8 some increase in durene levels are observed when applying the Zn-doped catalysts relative to the un-doped catalyst. However, in these examples durene selectivity are already so low (below 4 wt %) that it is without any significance to driveability.

In conclusion, examples 6-8 show that the incorporation of Zn to the zeolite increases the aromatics selectivity and the $C_{5+}$ yield, even so in the presence of hydrogen in the feed and that the presence of hydrogen in the feed leads to a reduction in the formation of durene and heavy oil. Thus, in a synthesis loop, finite amounts of hydrogen in the recycle stream is not necessarily prohibitive in regard to achieving the desired effects according to the present invention, namely that of increasing $C_{5+}$ yield and aromatics.

In the following the process and plant is further described with reference to the accompanying drawings. The drawings show exemplary embodiments of the present process and plant and are not to be construed as limiting to the scope of the present application.

FIG. 1 shows a schematic setup of a first embodiment according to the present invention, FIG. 2 shows a schematic setup of a second embodiment according to the present invention, and FIG. 3 shows a schematic setup of third embodiment according to the present invention.

FIG. 1 shows a schematic overview 1 of a plant/process according to the present application. A conversion effluent 2 is fed to a first separator 3 wherein the conversion effluent is separated into three streams: process condensate 4, first product stream 5 and a gas stream 6.

The first product stream is fed to a second separator 7 wherein the first product stream is separated into a second product stream 8 and a LPG stream comprising C3-C4 wherefrom the recycle stream 9a is taken.

As described herein the first product stream is near $H_2$ free and $H_2$ is present predominantly in the gas phase in the first separator. Thus when the first product stream is separated into the second product stream 8 and the recycle stream the recycle stream obtained is a $H_2$ depleted recycle.

The second product stream 8 may be send to further processing, upgrade, storage etc.

FIG. 2 shows a schematic overview 10 of a plant/process according to the present application. A conversion effluent 2 is fed to a first separator 3 wherein the conversion effluent is separated into three streams: process condensate 4, first product stream 5 and a gas stream 6. At least part of the gas stream 6 is taken through a $H_2$ depletion step 11 whereby a $H_2$ depleted recycle stream 9b obtained.

The $H_2$ depletion step 11 may comprise e.g. a $H_2$ permeable membrane and/or a catalytic oxidation step.

FIG. 3 shows a schematic overview 12 of a plant/process wherein the embodiments of FIGS. 1 and 2 are combined whereby a $H_2$ depleted stream is obtained from the gas stream 9b and from the LPG fraction taken from the second separator as $H_2$ depleted stream 9a.

In the embodiments of FIGS. 1, 2 and 3 the one or more $H_2$ depleted streams are returned to the conversion step (not shown) from which the conversion effluent 2 is obtained. The conversion step may be a MTG or a MTA process.

The invention claimed is:

1. A process for production of hydrocarbons comprising the steps of
converting a feed stream comprising alcohols, ethers or mixtures hereof over a bifunctional catalyst comprising zeolite, alumina binder and Zn, wherein the Zn is present at least partly as $ZnAl_2O_4$, in a conversion step thereby obtaining a conversion effluent including hydrogen,
separating said effluent to obtain an aqueous process condensate stream, a liquid hydrocarbon stream and a gaseous stream,
removing part of the hydrogen formed in the conversion step, and
recycling at least part of the gaseous and/or liquid hydrocarbon stream to the conversion step, wherein:
the at least partially H2 depleted recycle stream is obtained from the gaseous stream by passing said gaseous phase, after admixture with a predetermined amount of dioxygen, to a catalytic oxidation step, where hydrogen is reacted with said predetermined amount of oxygen to form water, and recycling said reacted stream, at least partly depleted in hydrogen, to the conversion step; and/or
the at least partly H2 depleted recycle stream is obtained from the gaseous stream by passing said gaseous phase, after admixture with a predetermined amount of a non-dioxygen hydrogen scavenger, to a catalytic oxidation step, where hydrogen is reacted with said predetermined amount oxidizing agent, and recycling said reacted stream, at least partly depleted in hydrogen, to the conversion step.

2. A process according to claim 1 wherein hydrogen is removed by purging at least part of the gaseous recycle stream.

3. A process according to claim 1 wherein an at least partially $H_2$ depleted recycle stream is obtained from the gaseous stream by passing the gaseous stream to a hydrogen permselective membrane.

4. A process according to claim 1, wherein the liquid hydrocarbon phase is separated into a product phase and one or more lower- and/or higher-boiling phases, at least one of which lower- and/or higher-boiling phases is at least partially recycled to the conversion step as the at least partly $H_2$ depleted recycle.

5. A process according to claim 1, wherein at least part of the gaseous phase is recycled to the conversion step.

6. A process according to claim 1, wherein the conversion step takes place in two or more consecutive reactors with quench addition of feed and recycle streams.

7. A process according to claim 3 wherein the permeation of $H_2$ in the selective membrane is adjusted to leave 1-10% of $H_2$ in the retentate, recycled to the conversion step as the at least partially $H_2$ depleted recycle stream.

8. A process according to claim 1, wherein the hydrogen scavenger is an aldehyde, wherein said aldehyde and hydrogen is converted into an alcohol over a hydrogenation catalyst.

9. A process according to claim 1, wherein the hydrogen scavenger is formaldehyde and wherein formaldehyde and hydrogen is converted into methanol over a hydrogenation catalyst.

10. A process according to claim 1, wherein the hydrogen scavenger is hydrogen peroxide and wherein hydrogen peroxide and hydrogen is converted into water over a hydrogenation catalyst.

11. A process according to claim 1, wherein the at least part of the recycle stream or recycle streams is returned to one or more points upstream the conversion step.

12. A process according to claim 1, comprising a step regulating the $H_2$ content in the at least partly $H_2$ depleted or partially depleted recycle stream.

13. A process according to claim 1, wherein the feed stream comprises methanol, dimethyl ether or mixtures hereof.

14. A process according to claim 1, wherein the process is carried out in one or more fixed bed reactors.

15. Process according to claim 1, wherein the catalyst is bifunctional catalyst and wherein the zeolite is ZSM-5 or ZSM-11.

16. Process according to claim 1, wherein the catalyst is bifunctional catalyst comprising 30-80% zeolite, 5-40% $ZnAl_2O_4$, 0-40% $Al_2O_3$, 0-10% ZnO.

17. Process according to claim 1, wherein the catalyst is bifunctional catalyst and wherein Zn is present in both zeolite and alumina binder.

18. Process according to claim 1, wherein the catalyst is bifunctional catalyst and wherein the alumina binder further comprises silica.

19. Process according to claim 1, wherein the catalyst is bifunctional catalyst and wherein the catalyst, by X-ray diffraction, does not contain free ZnO in the binder.

20. Process according to claim 1, wherein the catalyst is bifunctional catalyst and wherein the Zn concentration is 3-25 wt %.

21. Process according to claim 1, wherein the catalyst is bifunctional catalyst and wherein Zn is present in the binder as mainly $ZnAl_2O_4$.

22. Process according to claim 1, wherein the catalyst is bifunctional catalyst and wherein Zn is present in the binder as at least 50% $ZnAl_2O_4$.

23. Process according to claim 1, wherein the catalyst is bifunctional catalyst and wherein Zn is present in the binder as at least 95% $ZnAl_2O_4$.

24. Process according to claim 1, wherein the catalyst is bifunctional catalyst and wherein Zn is present in the binder as up to 10% ZnO.

25. Process according to claim 1, wherein the catalyst is bifunctional catalyst and wherein Zn in the zeolite is present as ZnO, Zn(OH)+ and/or Zn++ in ion exchange positions.

26. Process according to claim 1, wherein the catalyst is bifunctional catalyst and wherein the total Zn content in the catalyst is 3-25 wt % Zn.

27. Process according to claim 1, wherein the catalyst is bifunctional catalyst and wherein said catalyst is partly or fully spinelized.

28. Process according to claim 1, wherein the catalyst is bifunctional catalyst and wherein the Zn content is substantially the same in its partly spinelized and fully spinelized form.

29. Process according to claim 1, comprising a step of in situ obtaining a catalyst partially spinelized catalyst with a very high $ZnAl_2O_4$ content, fully spinelized catalyst or a substantially fully spinelized catalyst from a partially spinelized catalyst.

30. Product obtained by the process according to claim 1.

* * * * *